(12) United States Patent
Nehme et al.

(10) Patent No.: US 6,903,121 B1
(45) Date of Patent: Jun. 7, 2005

(54) TREATMENT OF TUMORS WITH ACETYLENES DISUBSTITUTED WITH A PHENYL OR HETEROAROMATIC GROUP AND A SUBSTITUTED CHROMANYL, THIOCHROMANYL OR TETRAHYDROQUINOLINYL GROUP IN COMBINATION WITH OTHER ANTI-TUMOR AGENTS

(75) Inventors: Alissar Nehme, Newport Beach, CA (US); Richard L. Beard, Newport Beach, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 451 days.

(21) Appl. No.: 09/640,852

(22) Filed: Aug. 17, 2000

(51) Int. Cl.$^7$ .................. A01N 43/40; A01N 43/54; A01N 43/58; A61K 31/44; A61K 31/50

(52) U.S. Cl. .................. 514/337; 514/247; 514/269

(58) Field of Search .................. 514/337, 247, 514/269

(56) References Cited

U.S. PATENT DOCUMENTS

| | | |
|---|---|---|
| 4,810,804 A | 3/1989 | Chandraratna .............. 514/311 |
| 4,980,369 A | 12/1990 | Chandraratna .............. 514/432 |
| 5,045,551 A | 9/1991 | Chandraratna .............. 514/337 |
| 5,089,509 A | 2/1992 | Chandraratna .............. 514/337 |
| 5,602,130 A | 2/1997 | Chandraratna .............. 514/247 |
| 6,028,088 A | 2/2000 | Pershadsingh et al. |
| 6,090,826 A | 7/2000 | Chandraratna .............. 514/337 |
| 6,114,348 A | 9/2000 | Weber et al. |

FOREIGN PATENT DOCUMENTS

| | | |
|---|---|---|
| EP | 01-10172 | 3/2002 |
| IE | 02-00001 | 7/2002 |
| US | 98-03355 | 8/1997 |
| US | 01-10410 | 10/2001 |

OTHER PUBLICATIONS

Nara, N. Leuk Lymphoma. Jun. 1993;10(3):201–7.*
Fanjul et al., Cancer Research 56, 1571–1577 (1996).
Toma et al., International Journal of Oncology 10: 597–607 (1997).
Kurbacher et al., Cancer Letters 103 (1996) 183–189.
Aapro et al., Cancer Chemother. Pharmacol. 10: 161–166 (1983).
Marth et al., J. Natl. Cancer Inst., 77: 1197–1202 (1986).
DiSepio et al., *Retinoic Acid Receptor–Nuclear Factor–Interleukin 6 Antagonism*, XP–001127433, The Journal of Biologial Chemistry, vol. No. 41, Issue of Oct. 10, pp 25555–25559 (1997).
Shi–Yong Sun and Reuben Lotan, *Retinoids as chemopreventive and therapeutic agents*, XP008010833, Drugs of the Future 1998, 23(6): 621–634 (1998).

* cited by examiner

*Primary Examiner*—Robert Landsman
(74) *Attorney, Agent, or Firm*—Robert J. Baran; Brent A. Johnson; Martin A. Voet (57) ABSTRACT

Compounds of Formula 1

Formula 1 where the symbols have the meaning described in the specification, and particularly the compound of Formula 3

Formula 3 (tazarotene)

exhibit synergistic anti-proliferative effect with human recombinant interferon in the treatment of solid tumors and leukemia, particularly breast cancer and acute myeloid leukemia.

9 Claims, 8 Drawing Sheets

_FIG. 15._

_FIG. 16._

TREATMENT OF TUMORS WITH ACETYLENES DISUBSTITUTED WITH A PHENYL OR HETEROAROMATIC GROUP AND A SUBSTITUTED CHROMANYL, THIOCHROMANYL OR TETRAHYDROQUINOLINYL GROUP IN COMBINATION WITH OTHER ANTI-TUMOR AGENTS

BACKGROUND OF THE INVENTION

1. Field of the Invention

The present invention relates to the use of acetylenes disubstituted with a phenyl or heteroaromatic group and a substituted chromanyl, thiochromanyl or tetrahydroquinolinyl group for the treatment of tumors in combination with other anti-tumor agents. More particularly the present invention relates to the use of ethyl 6-[2-(4,4-dimethylthiochroman-6-yl)ethynyl]nicotinate for the treatment of malignancies, particularly carcinoma of the breast and human myeloid leukemia, in combination with interferons and other anti-tumor agents.

2. Background Art

Naturally occurring retinoic acid and related compounds, generally called retinoids, have been known in the pharmaceutical, medical and related arts to have of important biological activity, including prevention and inhibition of malignant cell proliferation. A vast volume of patent and scientific literature exists describing the synthesis of retinoid compounds, their biological activities and investigations aimed at discovering the varying modes of action of retinoids in human and other biological systems, in vitro and in vivo as well.

Specifically, it is generally accepted in the art that in the anti-cell-proliferative or anti-tumor field, pharmaceutical compositions having a retinoid-like compound or compounds as the active ingredient are useful for treating or preventing hyperproliferative disorders of the skin, and other premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. Still more specifically, there are published reports in the art that certain retinoid compounds act additively and some even synergistically with other known anti-tumor chemotherapeutic agents, such as interferons and other drugs, in several carcinoma of the breast cell cultures to suppress or inhibit the proliferation of the cancer cells. The publication by Fanjul et al. in Cancer Research 56, 1571–1577 (1996) describes assays of several retinoid compounds, including a compound designated in the publication as SRI 11220 in combination with interferon in several carcinoma cell lines, and states that in some of the cell lines the anti-proliferative activity of the compound SRI 11220 and interferon was synergistic. The structure of this prior art compound SRI 11220 is shown below.

SRI 11220 (Prior Art)

SRI 11220 (Prior Art)

A publication by Toma et al. in International Journal of Oncology 10: 597–607 (1997) describes synergistic effects of certain other retinoids, such as all trans retinoic acid (tRA) with a interferon ($\alpha$ IFN) and synergistic effect with other chemotherapeutic agents such as tamoxifen (TAM) in MCF-7 human breast cancer lines. As further background to the present invention it is noted that a publication by Kurbacher et al. in Cancer Letters 103 (1996) 183–189 describes synergistic action of vitamin C with certain chemotherapeutic anti-tumor agents in MCF-7 and MDA-MB 231 human carcinoma cell lines.

U.S. Pat. Nos. 4,810,804, 4,980,369, 5,045,551, and 5,089,509 describe acetylenes disubstituted with a phenyl or heteroaromatic group and a substituted chromanyl, thiochromanyl or tetrahydroquinolinyl group having retinoid like activity. U.S. Pat. Nos. 5,602,130 and 6,090,826 disclose a method of treating diseases or conditions susceptible to treatment by retinoids, with acetylenes disubstituted with a heteroaromatic group and a substituted chromanyl, thiochromanyl or tetrahydroquinolinyl group. U.S. Pat. No. 5,089,509 is of particular relevance as background to the present invention, because it discloses the synthesis of ethyl 6-[2-(4,4-dimethylthiochroman-6-yl)ethynyl]nicotinate which is the preferred compound used in the method of treatment of the present invention. Ethyl 6-[2-(4,4-dimethylthiochroman-6-yl)ethynyl]nicotinate is also known by its trade name TAZAROTENE®, and is often referred to in the present specification (including the drawing figures) simply as "tazarotene".

SUMMARY OF THE INVENTION

The present invention relates to the use of the compounds of Formula

Formula 1 where X is S or O, and $R_1$ is, independently, H or lower alkyl of 1 to 6 carbons; H or lower alkyl of 1 to 6 carbons;

$R_2$ and $R_3$ are independently H, lower alkyl of 1 to 6 carbons, F, Cl, Br, I, alkoxy of 1 to 6 carbons, or fluoroalkoxy of 1 to 6 carbons;

m is an integer 0 to 3;

o is an integer 0 to 4;

n is 0–5;

Y is phenyl, naphthyl, or a heteroaryl group selected from a group consisting of pyridyl, thienyl, furyl, pyridazinyl, pyrimidinyl, pyrazinyl; oxazolyl, thiazolyl, or imidazolyl, and B is COOH, a pharmaceutically acceptable salt thereof, $CONR_6R_7$ or $COOR_8$ where $R_6$ and $R_7$ independently are hydrogen or an alkyl group of 1 to 6 carbons and $R_8$ is alkyl of 1 to 6 carbons, for the treatment of a malignant tumor or condition in a mammal in need of such treatment, in combination with one or more other anti-tumor agent, preferably in combination with an interferon.

COMPOUNDS USED IN THE METHODS OF TREATMENT OF THE INVENTION

The general formula of the compounds used in the methods of treatment of the invention is shown in Formula 1. Among the compounds shown in that formula, the use of those are preferred where the variable Y designates pyridine. Even more preferred are those where the pyridine moiety is 2,5 substituted. (Substitution in the 2,5 positions in the "pyridine" nomenclature corresponds to substitution in the 6-position in the "nicotinic acid" nomenclature.) As far as the $(CH_2)_n$ group is concerned, compounds are preferred where n is 0. Preferably B is COOH or $COOR_8$ where $R_8$ is lower alkyl of 1 to 3 carbons. $R_1$ preferably designates H or methyl, and $R_2$ and $R_3$ are preferably H or lower alkyl. The variable X preferably represents S or O, still more preferably S.

A more preferred group of compounds utilized in the methods of the invention is depicted by Formula 2

FORMULA 2

Formula 2 where $R_1$ is H or methyl, $R_3$ is H or methyl, and $R^*_8$ is H, or lower alkyl of 1 to 3 carbons, or a pharmaceutically acceptable salt of said compound. The compounds of Formula 1 and of Formula 2 can be obtained in accordance with the synthetic procedures described in U.S. Pat. Nos. 4,810,804, 4,980,369, 5,045,551, and 5,089,509, each of which is expressly incorporated herein by reference.

The presently most preferred compound used in the methods of treatment of the present invention is ethyl 6-[2-(4,4-dimethylthiochroman-6-yl)ethynyl]nicotinate (tazarotene) the structure of which is disclosed by Formula 3. Tazarotene is described as example 6 in the specification of U.S. Pat. No. 5,089,509.

Formula 3 (tazarotene)

It should be understood in connection with the description of the compounds used in the methods of treatment of the present invention that a pharmaceutically acceptable salt is any salt which retains the activity of the parent compound and does not impart any deleterious or untoward effect on the subject to which it is administered and in the context in which it is administered. Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

It should be further understood in connection with the description of the compounds used in the methods of treatment of the present invention that in Formulas 1 and 2, the substituents $R_2$ and $R_3$ are optional, meaning that when the variables m and o have the value of 0 (zero), then the respective ring is hydrogen substituted; in other words the ring bears no $R_2$ or $R_3$ substituent other than hydrogen.

The anti-proliferative effects of the compounds used in accordance with the invention are demonstrated by assay procedures well accepted in the art. These assays are performed on the preferred compound, tazarotene (the compound of Formula 3) without and also in combination with human recombinant $\alpha$, $\beta$ and $\gamma$ interferon which are anti-tumor agents well known in the art. The materials and the assays procedures are described in detail below.

The SK-BR-3, T47D and HL-60 cell cultures in which the assay procedures were performed are also well known and are available from sources well known in the art. Specifically, as is known, T47D is an estrogen receptor positive ($ER^+$) human breast cancer cell line, and SK-BR-3 is an estrogen receptor negative ($ER^-$) human breast cancer cell line. HL-60 is a well known human myeloid leukemia cell line. The assay procedure for the breast cancer lines itself is well known in the art and involves determining incorporation of 5-bromo-2'-deoxyuridine (BrdU) into the cells. As is known, incorporation of less BrdU represents less cell proliferation (inhibition of cell proliferation), and this assay is accepted in the art as a measure of anti-proliferative or anti-tumor activity of the assayed agent or agents. The assay procedure for the HL-60 cell line is also well-known in the art. It involves measuring the concentration of formazan dye which is cleaved from 3-[4,5-dimethylthiazole-2-yl]-2,5-diphenyltetrazolium bromide by viable HL-60 cells.

When a combination of two or more anti-proliferative or potentially anti-proliferative agents is assayed, the results may indicate less inhibition of proliferation than what we would be expected if the effects of the individual agents were additive, or the effects may represent the mathematical product of the expected effects of the two agents (additive inhibition). Alternatively, the inhibition actually observed experimentally may be greater than what would be expected as a simple product of the effects of the two agents. Such synergistic anti-tumor or antiproliferative effect is highly desirable, and as is described below was observed in several assays when tazarotene (Formula 3) was used in combination with human recombinant interferon. This synergistic effect of the compounds used in the invention with interferon in the treatment of malignancies, and especially in treatment of breast cancer and of acute human myeloid leukemia is not expected based on the prior art and is unobvious and surprising. The materials and procedures of the assays as well as the mathematical criteria for determining synergistic effects are described below.
Materials, Assay Methods and Criteria for Determining Synergism Reagents The human recombinant interferon-alpha (IFN-$\alpha$) and human recombinant interferon-beta (IFN-$\beta$) were purchased from Sigma Chemicals Co. (St Louis, Mo.). Human recombinant interferon-gamma (IFN-$\gamma$) was purchased from Roche Diagnostics (Indianapolis, Ind.). The stock solutions were stored at −70, 4, and −20° C. for IFN-$\alpha$, IFN-$\beta$ and IFN-$\gamma$, respectively. IFN working solutions were prepared before use by dilutions in the culture medium. 5 mM stock solution for tazarotene (Formula 3) was prepared in DMSO, which was subsequently diluted in culture medium to the indicated final concentration.
Culture of Breast Cancer Cell Lines The estrogen receptor-positive ($ER^+$) cell line T-47D and the $ER^-$ cell line SK-BR-3 were cultured in Dulbecco's modification of Eagle's medium (DMEM Gibco BRL, Gaithersburg, Md.) supplemented with 10% fetal bovine serum (HyClone, Logan, Utah), 2 mM L-glutamine and 1% antibiotics-antimycotics (Gibco BRL). Cell lines were obtained from the American Type Culture Collection (ATCC, Rockville, Md., HTB-133 and HTB-30 for T-47D and SK-BR-3, respectively). Cells were cultured at 370C in a humidified atmosphere containing 5% $CO_2$.
Culture of HL-60 Acute Myeloid Leukemia Cells The human myeloid leukemia cell line HL-60 was cultured in Iscove's modified Dulbecco's medium (IMDM Gibco BRL, Gaithersburg, Md.) supplemented with 10% fetal bovine serum (HyClone, Logan, Utah), 2 mM L-glutamine and 1% antibiotics-antimycotics (Gibco BRL). HL-60 cells were obtained from the American Type Culture Collection (ATCC, Rockville, Md., CCL-240). Cells were cultured at 37° C. in a humidified atmosphere containing 5% $CO_2$.
Cell Proliferation Assay in Breast Cancer Cell Lines Proliferation of cancer cell lines was determined using a commercial cell proliferation kit (Roche Diagnostics), essentially following the instructions of the manufacturer. Cells were seeded into 96-well tissue culture plates (Corning Incorporated, Corning, N.Y.) at a concentration of 3000 cells/well. After 24 hours, cells were treated continuously with tazarotene (Formula 3) and/or interferons (IFNs) or solvent alone. The appropriate concentrations of tazarotene (Formula 3) used in this study were between $10^{-11}$ M and $10^{-6}$M; IFN concentrations were between 10 and 1000 Unit/ml. Culture media were changed every 72 hours. After 7 days, 10 $\mu$l of 5-bromo-2'-deoxyuridine (BrdU) was added to each well. Incubation with BrdU was stopped 24 hours later by adding 100 $\mu$l of anti-BrdU antibody to each well. The amount of BrdU incorporated into the DNA of proliferating cells was assessed by measuring absorbance at 450 $\mu$m. Each experiment was performed in triplicate in three independent experiments.
Cell Proliferation Assay (MTT) in HL-60 Leukemia Cell Line Proliferation of the HL-60 leukemia cell line was determined by a cell viability and non-radioactive commercial cell proliferation kit (MTT assay; Roche Diagnostics, Indianapolis, Ind.), essentially by following the instructions of the manufacturer. Cells were seeded into 96-well tissue culture plates (Corning Incorporated, Corning, N.Y.) at a concentration of 1000 cells/well. After 24 hours, the cells were treated continuously with tazarotene (Formula 3) and/or IFNs or solvent alone. The appropriate concentrations of tazarotene (Formula 3) used in this study were between $10^{-11}$ M and $10^{-6}$M; IFN concentrations were between 0.1 and 1000 Unit/ml. Culture media were changed every 72 hours. After 6 days, 10 $\mu$l of MTT (3-[4,5-dimethylthiazole-2-yl]-2,5-diphenyltetrazolium bromide) was added to each well. The reaction was stopped after 4 hours of incubation by adding 100 μl of 10% SDS in 0.01 M HCl. The quantification of viable cells, capable of cleaving MTT to form a formazan dye, was assessed by measuring absorbance at 590 nm. All determinations were performed in triplicate in three independent experiments.

Criteria for Synergism

The growth inhibition observed for a combined treatment with tazarotene (Formula 3) and IFNs was analyzed for both synergistic and additive effects. The criteria for these effects have been discussed by three different groups (Aapro et al., Cancer Chemother. Pharmacol., 10: 161–166, 1983, Marth et al. J. Natl Cancer Inst., 77:1197–1202, 1986, Kurbacher et al., Cancer Letters, 103: 183–189, 1996). The mathematical multiplication of the two surviving fractions after the treatment of either with tazarotene (Formula 3) or with the respective interferon is the calculated value for simple additivity of both agents in combination. This calculated value is compared to the actual value observed to determine the nature of the combination effect. Statistical significance of synergistic effects is determined by using the two-sided Student's t-Test. Synergism or inhibition was determined for each experiment individually, with the P value being 0.05 in comparison to the simple additivity hypothesis. Table 1 below shows the mathematical expressions for the criteria of two agents being synergistic, additive, subadditive and antagonistic, respectively.

TABLE 1

Definitions of drug combination effects[a]

| | |
|---|---|
| Synergistic | $SF_{A+B} < (SF_A) \times (SF_B)$ |
| Additive | $SF_{A+B} = (SF_A) \times (SF_B)$ |
| Subadditive | $SF_{A+B} > (SF_A) \times (SF_B)$ |
| | And $<SF_B$ when $SF_A > SF_B$ |
| Antagonistic | $SF_{A+B} > (SF_A) \times (SF_B)$ |

[a]$SF_A$: Surviving fraction from treatment A;
$SF_B$: Surviving fraction from treatment B;
$SF_{A+B}$: Surviving fraction from treatment A plus B.

Anti-Proliferative Effects Determined by the Assays

Referring now to the graphs of FIGS. 1 through 16, each of these represents the results obtained in the above described assays where SK-BR-3, T-47D and HL-60 cells, respectively, were treated with a combination of tazarotene (Formula 3) and human recombinant interferon (IFN) α, β, and γ, respectively. In the graphs of FIGS. 1–12, pertaining to assays with SK-BR-3 cells and T-47D cells, the incorporation of 5-bromo-2'-deoxyuridine (BrdU) is plotted on the Y (vertical) axis and varying concentration of tazarotene (Formula 3) or varying concentration of IFNa. IFNβ or of IFNγ, respectively, is plotted on the X (horizontal) axis. The concentration of the interferons is expressed in international units, as is accepted in the art, whereas the molar concentration of tazarotene (Formula 3) is plotted on a logarithmic scale. Each graph includes a curve indicating results with one agent only, actual experimental results with the combination of the two agents (tazarotene and the respective interferon), and a theoretical curve which is calculated in the manner described above, assuming for the calculation that the effects of the two agents would be simply additive. The incorporation of BrdU is plotted on a percentage basis relative to the situation when the agent of varying concentration in the respective graph was not used (O concentration represents 100% incorporation). The graphs of FIGS. 13–16 are analogous, except that in these graphs the quantity of viable cells capable of cleaving MTT to form formazan dye, as measured by the quantity of fomazan dye (itself measured by absorbance at 590 nm) is plotted on the vertical (Y) axis. Referring now specifically to the graph if FIG. 1, in the assay of SK-BR-3 cells depicted in that graph the concentration of IFNα was 100 International Units (U) per ml, and the concentration of tazarotene was varied. It can be seen on the graph that the experimentally or actually observed inhibition of cell proliferation was significantly greater (less BrdU incorporation) than with IFNa alone, and significantly greater than the theoretically additive curve, thus showing a synergistic effect of tazarotene (Formula 3) and IFNα . . . The graphs of FIGS. 3 and 5, similarly depict the results of assays in SK-BR-3 cells where the concentration of IFNβ or IFNγ was kept constant at 10U/ml and at 100U/ml respectively, and the concentration of tazarotene (Formula 3) was varied. The graphs of FIGS. 3 and 5 also show significant synergistic effect of the combination treatment. The graphs of FIGS. 7, 9, and 11 again disclose the results of assays with SK-BR-3 cells. In these assays the concentration of tazarotene (Formula 3) was kept constant at 10 nM, and the concentration of IFNα, IFNβ or IFNγ was varied between 0 to 1000 International Units (0 to 1000 U) per milliliter (ml). These graphs reveal striking synergism. The graphs of FIGS. 2, 4 and 6 disclose the results of assays with T-47D cells, where in analogy to the assays shown in graphs of FIGS. 1, 3 and 5 the concentration of tazarotene (Formula 3) was varied, and the concentration of IFNt, IFNβ or IFNγ was kept constant at 100 U/ml. The graphs of these figures also shows synergism, although not as striking as in the assays with SK-BR-3 cells.

Figure 1:
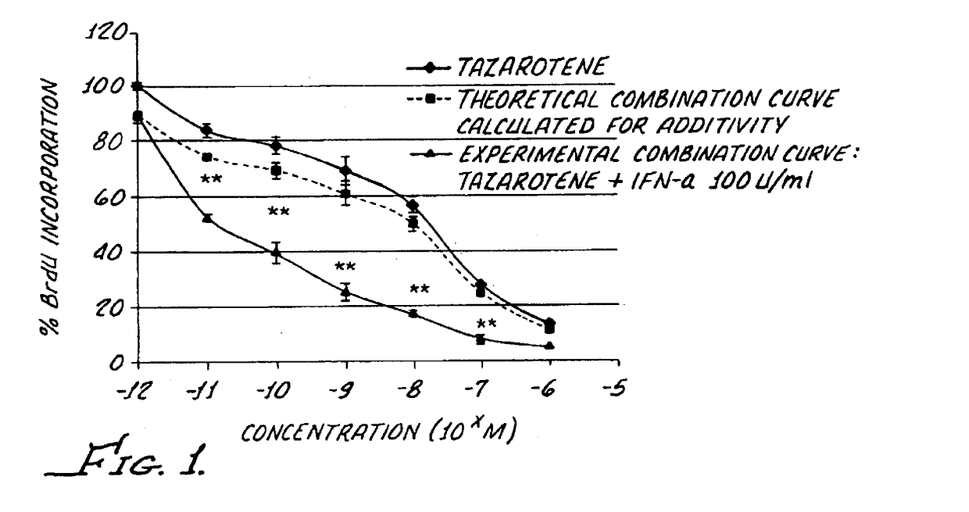
FIG. 1 is a graph showing synergism in the anti-proliferative effects of a combination of the compound tazarotene (Formula 3) and of α interferon (IFN-a or IFNα) in SK-BR-3 cells.
Figure 2:
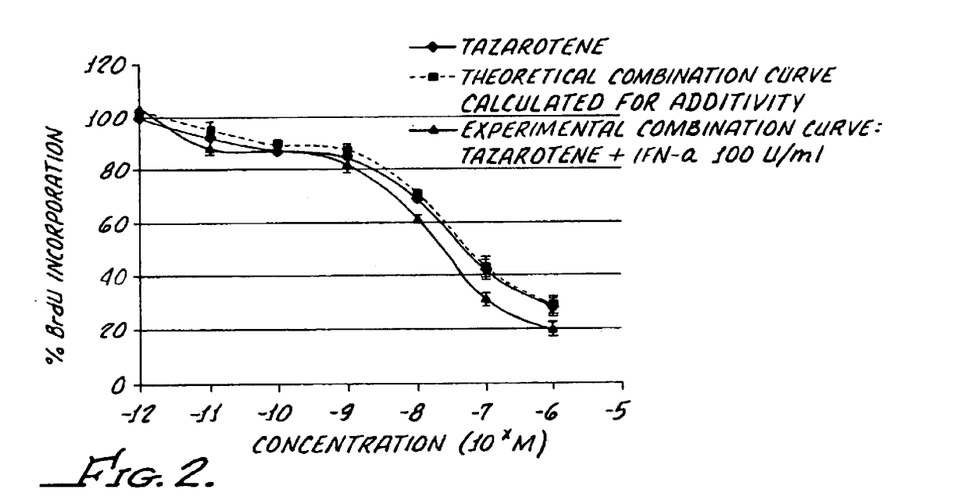
FIG. 2 is a graph showing the anti-proliferative effects of a combination of the compound tazarotene (Formula 3) and of a interferon (IFN-a or IFNα) in T-47D cells.
Figure 3:
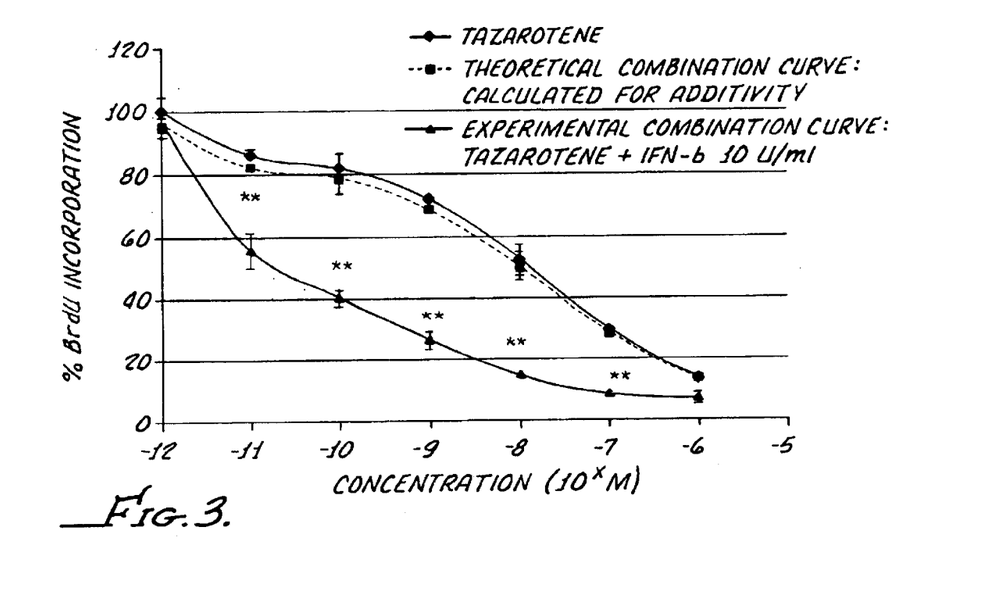
FIG. 3 is a graph showing synergism in the anti-proliferative effects of a combination of the compound tazarotene (Formula 3) and of β interferon (IFN-b or IFNβ) in SK-BR-3 cells.
Figure 4:
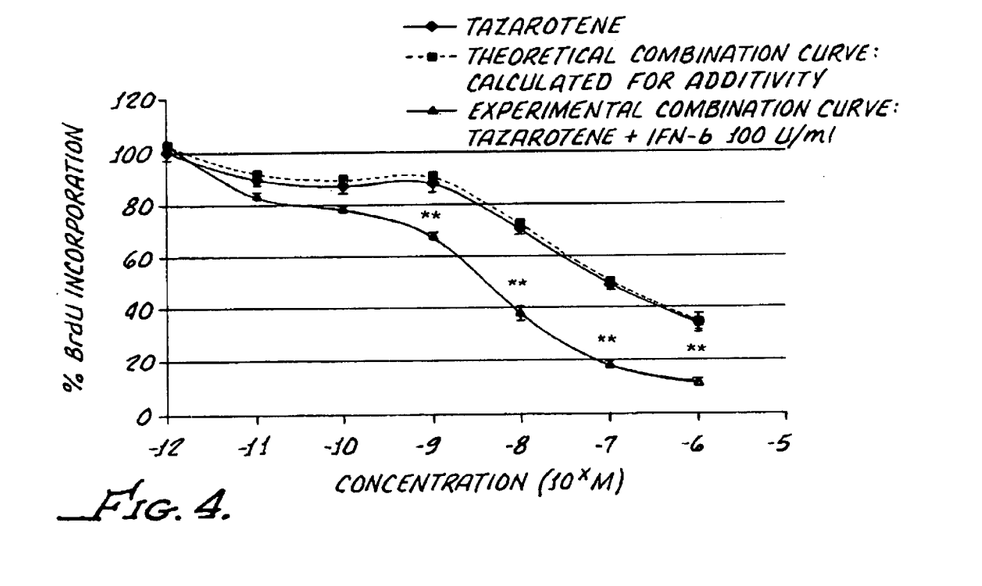
FIG. 4 is a graph showing synergism in the anti-proliferative effects of a combination of the compound tazarotene (Formula 3) and of interferon (IFN-b or IFNβ) in T-47D cells.
Figure 5:
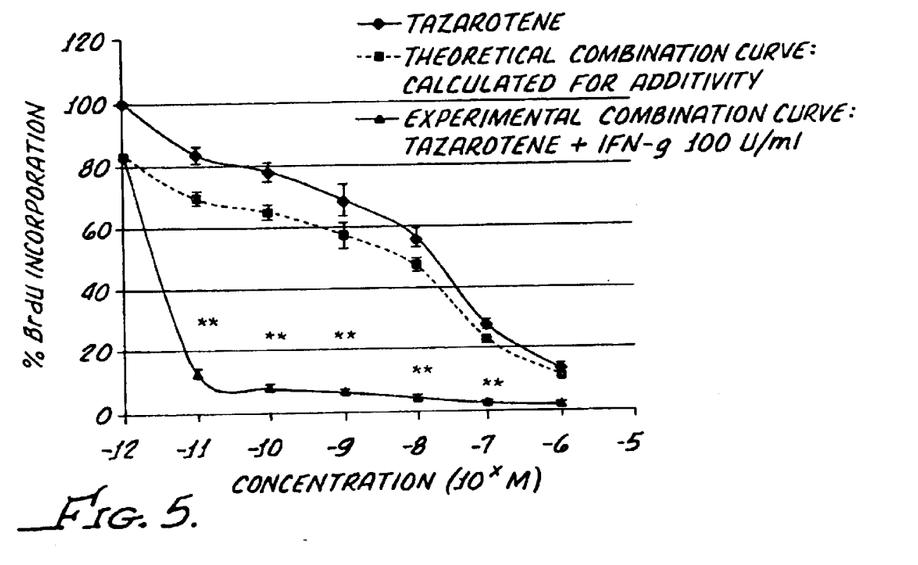
FIG. 5 is a graph showing synergism in the anti-proliferative effects of a combination of the compound tazarotene (Formula 3) and of γ interferon (IFN-g or IFNγ) in SK-BR-3 cells.
Figure 6:
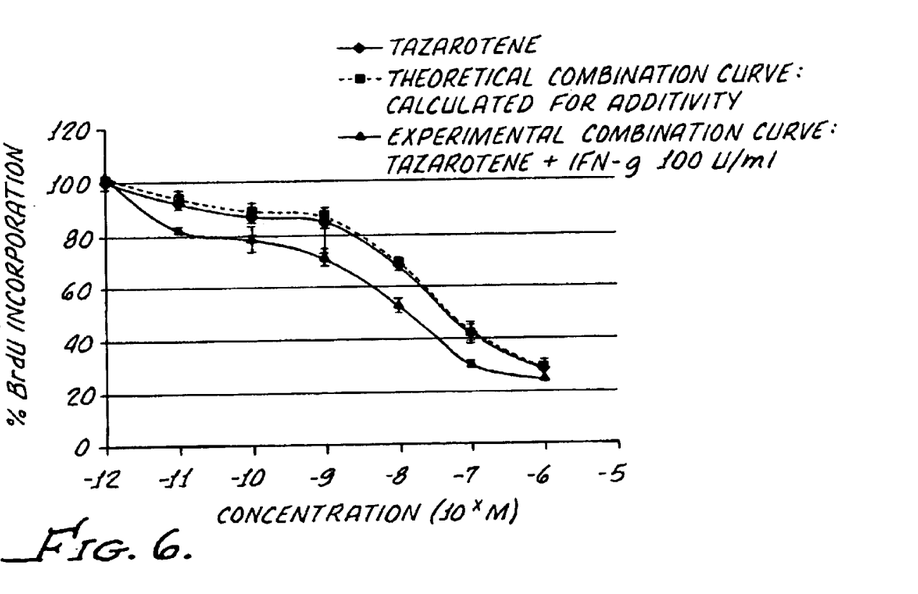
FIG. 6 is a graph showing the anti-proliferative effects of a combination of the compound tazarotene (Formula 3) and of y interferon (IFN-g or IFNγ) in T-47D cells.
Figure 7:
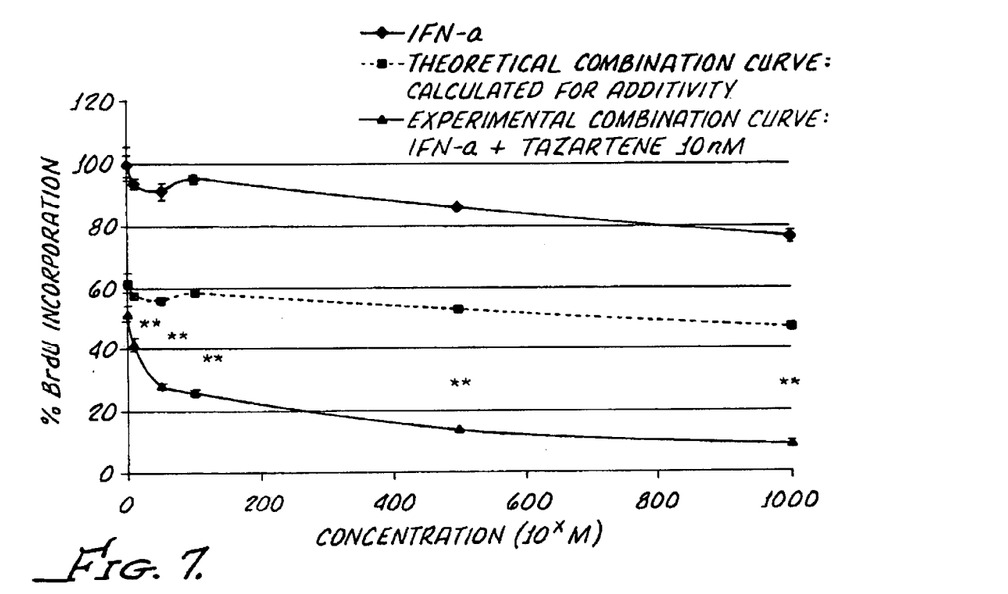
FIG. 7 is another graph showing synergism in the anti-proliferative effects of a combination of the compound tazarotene (Formula 3) and of a interferon (IFN-a or IFNα) in SK-BR-3 cells.
Figure 8:
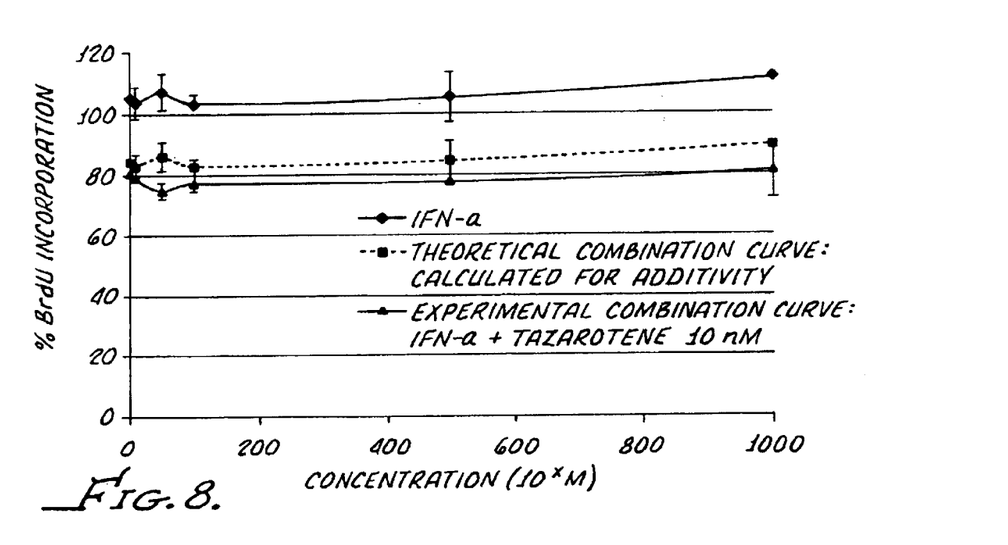
FIG. 8 is another graph showing the anti-proliferative effects of a combination of the compound tazarotene (Formula 3) and of α interferon (IFN-a or IFNα) in T-47D cells.
Figure 9:
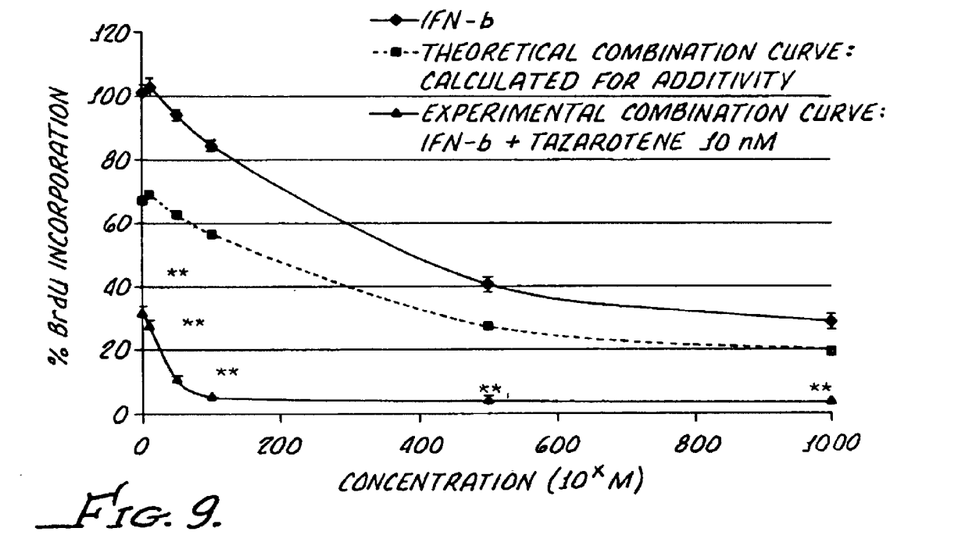
FIG. 9 is another graph showing synergism in the anti-proliferative effects of a combination of the compound tazarotene (Formula 3) and of β interferon (IFN-b or IFNβ) in SK-BR-3 cells.
Figure 10:
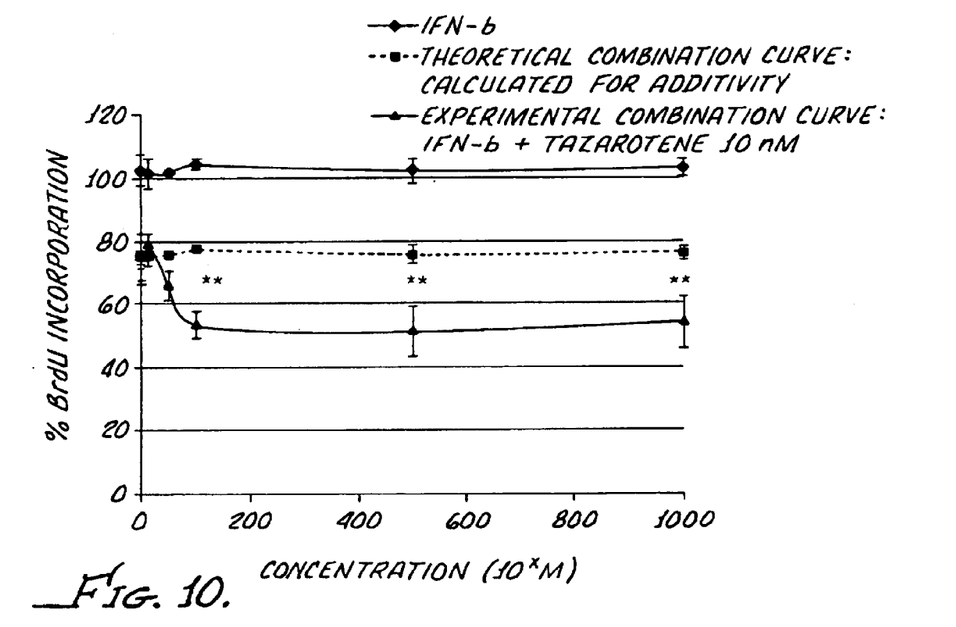
FIG. 10 is another graph showing synergism in the anti-proliferative effects of a combination of the compound tazarotene (Formula 3) and of β interferon (IFN-b or IFNβ) in T-47D cells.
Figure 11:
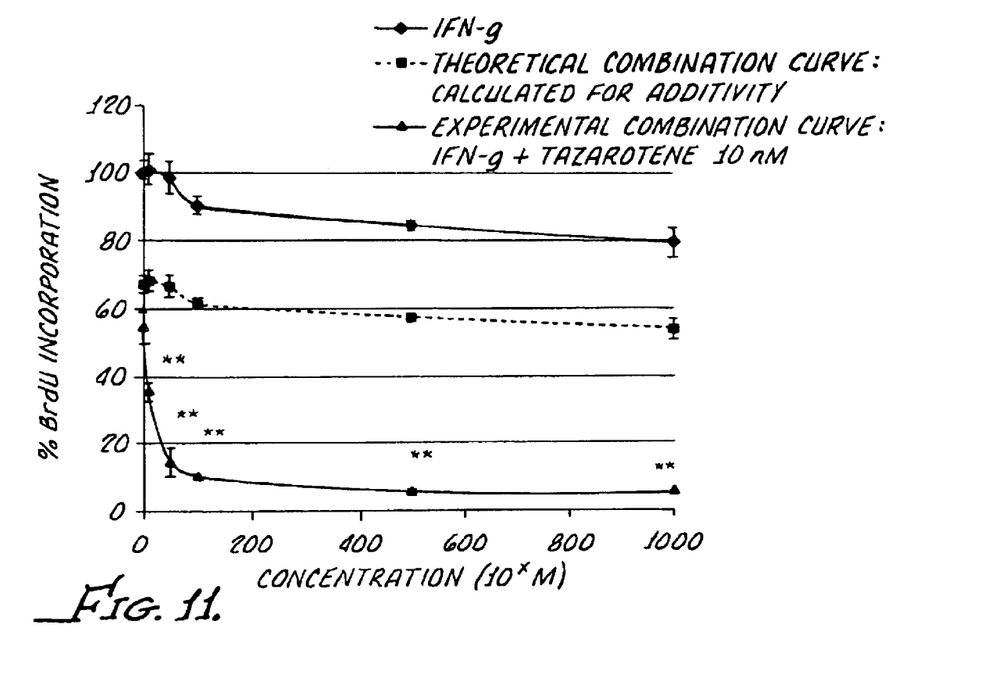
FIG. 11 is another graph showing synergism in the anti-proliferative effects of a combination of the compound tazarotene (Formula 3) and of γ interferon (IFN-g or IFNγ) in SK-BR-3 cells.
Figure 12:
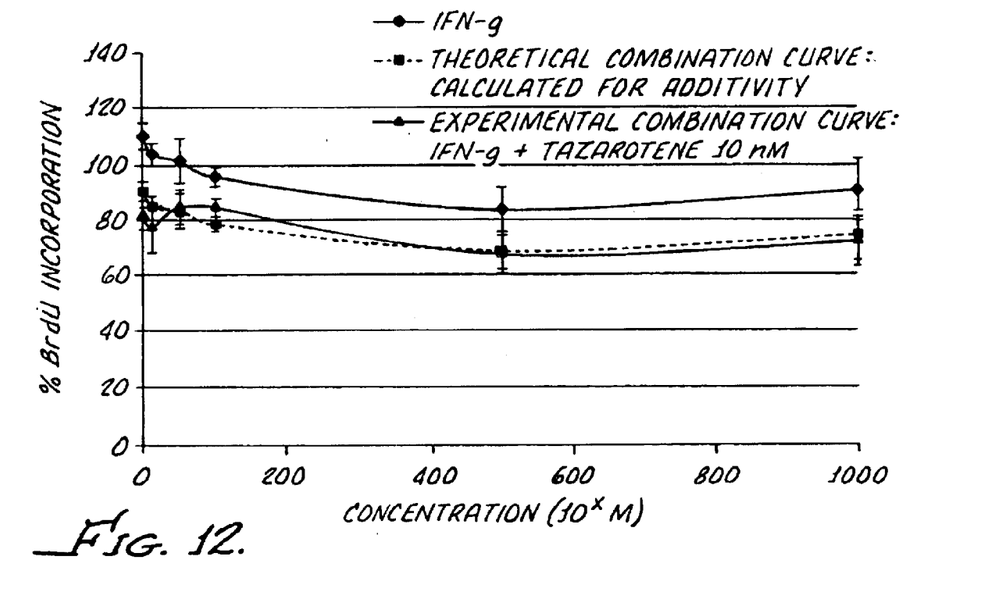
FIG. 12 is another graph showing the anti-proliferative effects of a combination of the compound tazarotene (Formula 3) and of y interferon (IFN-g or IFNγ) in T-47D cells.
Figure 13:
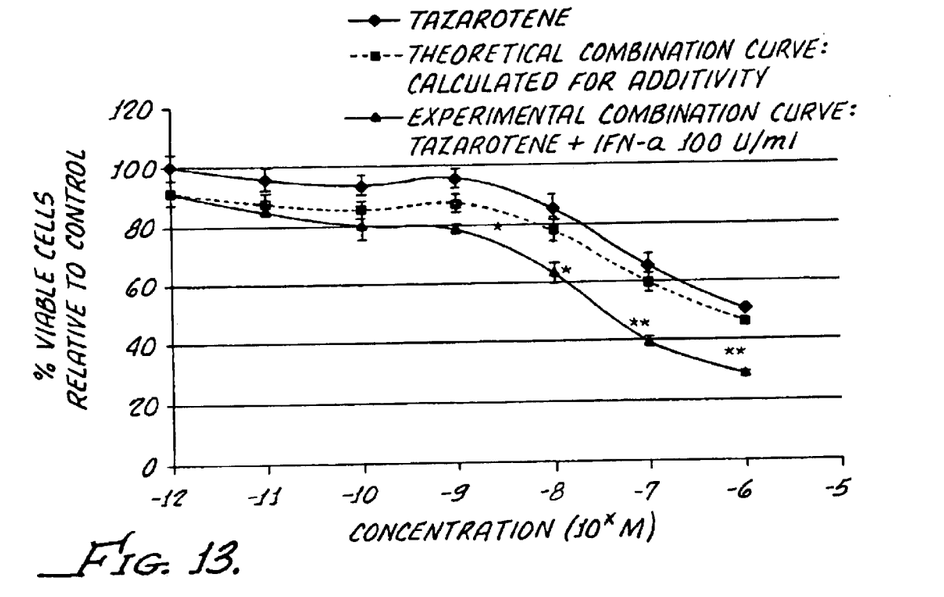
FIG. 13 is a graph showing synergism in the anti-proliferative effects of a combination of the compound tazarotene (Formula 3) and of β interferon (IFN-alpha or IFNα) in HL-60 cells.
Figure 14:
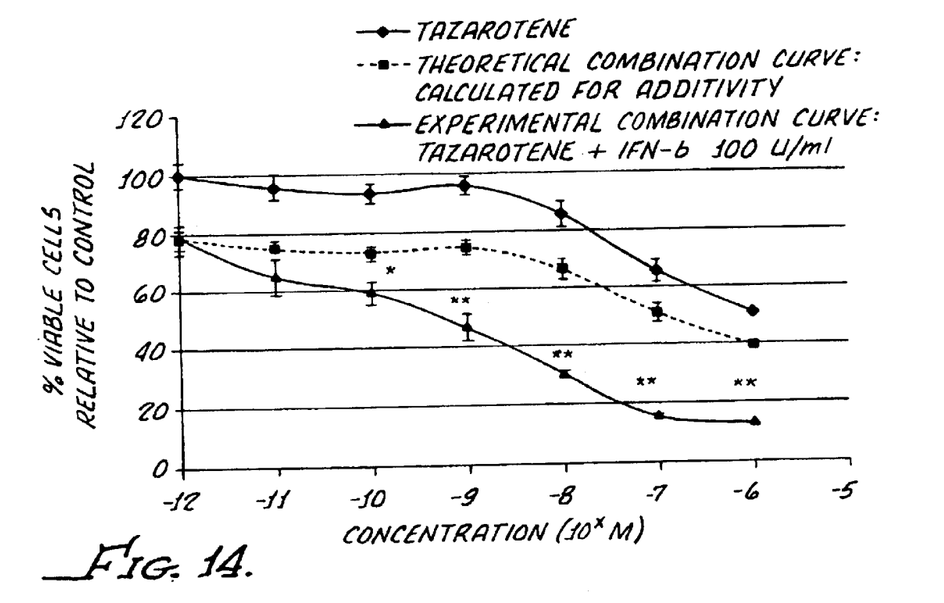
FIG. 14 is a graph showing synergism in the anti-proliferative effects of a combination of the compound tazarotene (Formula 3) and of β interferon (IFN-beta or IFNβ) in HL-60 cells.
Figure 15:
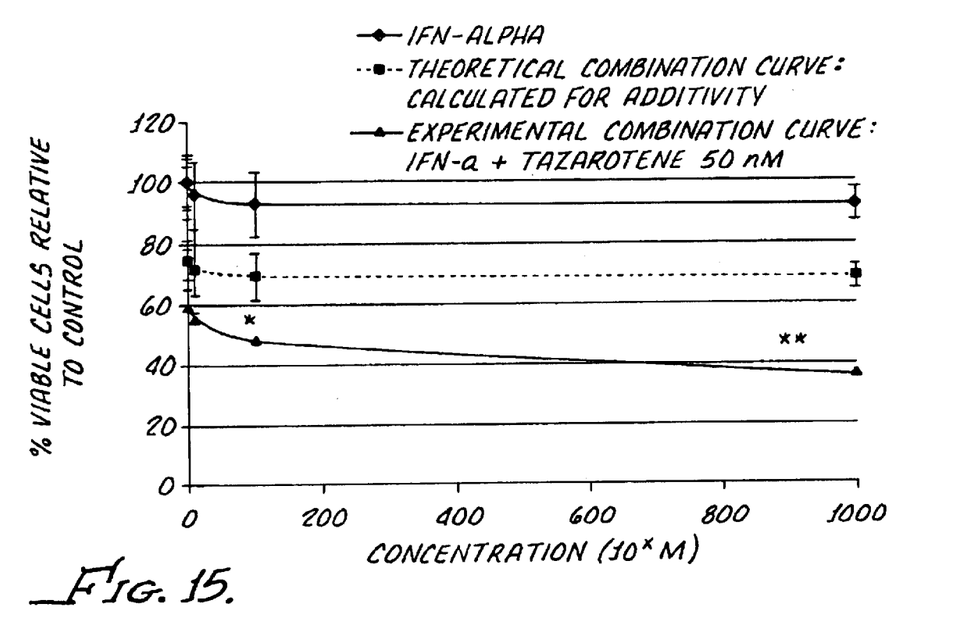
FIG. 15 is another graph showing synergism in the anti-proliferative effects of a combination of the compound tazarotene (Formula 3) and of β interferon (IFN-alpha or IFNα) in HL-60 cells.
Figure 16:
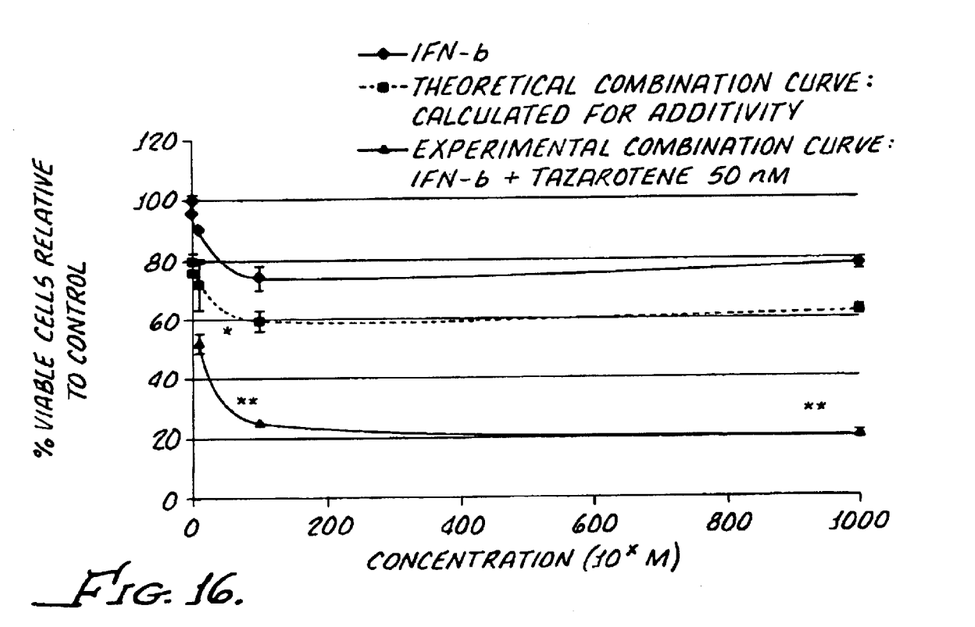
FIG. 16 is another graph showing synergism in the anti-proliferative effects of a combination of the compound tazarotene (Formula 3) and of β interferon (IFN-beta or IFNβ) in HL-60 cells.

The graphs of FIGS. 8, 10 and 12 also disclose the results of assays with T-47D cells. In these assays, in analogy to the assays shown in graphs of FIGS. 7, 9 and 11, the concentration of tazarotene (Formula 3) was kept constant at 10 nM, and the concentration of IFNα, IFNβ or IFNγ was varied between 0 to 1000 International Units (0 to 1000 U) per milliliter (ml). The graph of FIG. 8 (IFNα) reveals weak synergism, and the graph of FIG. 10 (IFNβ) shows significant synergism.

FIGS. 13–16 pertain to assays with HL-60 acute myeloid leukemia cells. In the assays disclosed by FIGS. 13 and 14, the concentration of IFNα or IFNβ was kept consntant at 100 U/ml, and the concentration of tazarotene (Formula 3) was varied. In the assays disclosed by the graphs of FIGS. 15 and 16 the concentration of tazarotene (Formula 3) was kept constant at 50 nM, and the concentration of IFNα or IFNβ, respectively, was varied between 0 to 1000 U/ml. In these assays also, significant synergism was observed.

The foregoing results and particularly the synergism in the anti-proliferative effects on the two solid tumor cancer cell lines and in the HL-60 leukemia cells of tazarotene (Formula 3) and of human recombinant interferon is unexpected, surprising, and an indication that the compounds of Formula 1 are useful for the treatment of diseases involving malignant cell-proliferation, such as solid tumors, particularly carcinoma of the breast, and leukemias, particularly acute myeloid leukemia. In fact, the foregoing assays indicated that the compounds of Formula 1 are useful in combination therapy with interferon in breast cancer cell lines which are estrogen receptor positive (T-47D) and also in human breast cancer cell lines which are estrogen receptor negative (SK-BR-3).

Methods of Treatment, Modes of Administration

The compounds of Formula 1 may be administered systemically or topically, depending on such considerations as the condition to be treated, need for site-specific treatment, quantity of drug to be administered, and numerous other considerations. For the treatment of breast cancer and many other forms of solid tumors, as well as in treatment of leukemias, the compounds of Formula 1 are more likely to be administered systemically, in a pharmaceutical composition containing such excipients or inert components which are well known in the art pertaining to chemotherapy of tumors. More specifically, if a compound of Formula 1 is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain other cases, it may be useful to formulate these compounds in suppository form or as extended release formulation for deposit under the skin or intramuscular injection.

The compound of Formula 1 will be administered as a chemotherapeutic agent for treatment of tumors in a useful therapeutic dose which will vary from condition to condition and in certain instances may vary with the severity of the condition being treated and the patients susceptibility to treatment. Accordingly, no single dose will be uniformly useful, but will require modification depending on the particularities of the tumor or malignancy being treated. Such doses can be arrived at through routine experimentation. For the treatment of solid tumors and leukemias, particularly breast cancer and acute myeloid leukemia, it is anticipated that the compound of Formula 1 will be administered for approximately 1 to 8 weeks to a patient in need thereof, in a dose that is effective to halt, slow the growth or dissipate the tumor or halt leukemia cell proliferation. Preferably, the compound is to be administered orally, in a daily dose which preferably will be in the range of a approximately 50 mg per day to 500 mg per day. Most preferably the compound used in the treatment will be tazarotene (Formula 3). Preferably the compounds of Formula 1, and most preferably tazarotene (Formula 3) will be administered in combination with other chemotherapeutic agents, such as interferons, preferably human recombinant interferon, or other known chemotherapeutic agents of malignancies. Other chemotherapeutic agents with which the compounds of Formula 1 are likely to be used in combination therapy are tamixofen and taxol. With the use of interferons and with certain other chemotherapeutic agents as well, a synergistic anti-proliferative, anti-tumor effect is likely to occur, as is demonstrated by the above described cell culture assay procedures. Again, when the compounds of Formula 1 are used in a combination therapy, the useful therapeutic dose will vary from condition to condition and in certain instances may vary with the severity of the condition being treated and the patient's susceptibility to treatment. Accordingly, the required dose will be arrived at through routine experimentation, which is customary in the science of the chemotherapy of malignancies. Generally speaking it is contemplated that in combination therapy and for the treatment of solid tumors and leukemias, the daily dose of the compound of Formula 1 will be in the range of a approximately 50 mg per day to 500 mg per day. The daily dose of the other chemotherapeutic agent or agents given in combination with the compound of Formula 1 will depend on the nature of the chemotherapeutic agent or agents, and can be arrived by routine experimentation normally practiced in the art. When interferon is used for the treatment of solid tumors or leukemias, such as for example breast cancer or acute myeloid leukemia, in combination with the compounds of Formula 1, then the daily dose of the interferon is likely to be in the range of approximately 1 to 9 million international units per day.

What is claimed is:

1. A pharmaceutical composition for the treatment of a malignant disease or condition in a mammal, said disease or condition being selected from the group consisting of breast cancer, colon cancer and leukemia, the composition comprising a pharmaceutically acceptable excipient and a therapeutically effective dose of a compound of the formula where X is S or O;

$R_1$ is, independently, H or lower alkyl of 1 to 6 carbons;

$R_2$ and $R_3$ are, independently, H, lower alkyl of 1 to 6 carbons, F, Cl, Br, I, alkoxy of 1 to 6 carbons, or fluoroalkoxy of 1 to 6 carbons;

m is an integer 0 to 3;

o is an integer 0 to 4;

n is 0–5;

Y is phenyl, naphthyl, or a heteroaryl group selected from a group consisting of pyridyl, thienyl, furyl, pyridazinyl, pyrimidinyl, pyrazinyl; oxazolyl, thiazolyl, or imidazolyl; and B is COOH, a pharmaceutically acceptable salt thereof, $CONR_6R_7$ or $COOR_8$ where $R_6$ and $R_7$, independently, are hydrogen or an alkyl group of 1 to 6 carbons and $R_8$ is alkyl of 1 to 6 carbons;

said composition to be used in combination with interferon.

2. A pharmaceutical composition for the treatment of a malignant disease or condition in a mammal, said, disease or condition being selected from the group consisting of breast cancer and leukemia, the composition comprising a pharmaceutically acceptable excipient and a therapeutically effective dose of a compound of the formula where $R_1$ is H or methyl, $R_3$ is H or methyl, and $R^*_8$ is H, or lower alkyl of 1 to 3 carbons; or a pharmaceutically acceptable salt of said compound, said composition to be used in combination with interferon.

3. A pharmaceutical composition for the treatment of a malignant disease or condition in a mammal, said disease or condition being selected from the group consisting of breast cancer and leukemia, the composition comprising a pharmaceutically acceptable excipient and a therapeutically effective dose of a compound of the formula where $R_8$ is H, alkyl of 1 to 3 carbons, or a pharmaceutically acceptable salt of said compound, said composition being adapted to be used in combination with another chemotherapeutic agent effective for the treatment of the malignant disease or condition of the mammal wherein said composition in combination with interferon.

4. A method of treating a malignant disease or condition in a mammal in need of such treatment, said condition being selected from the group consisting of breast cancer and leukemia, the method comprising the steps of:
administering to said mammal a pharmaceutical composition comprising a pharmaceutically acceptable excipient and a therapeutically effective dose of a compound of the formula where X is S or O;
$R_1$ is, independently, H or lower alkyl of 1 to 6 carbons;
$R_2$ and $R_3$ are, independently, H, lower alkyl of 1 to 6 carbons, F, Cl, Br, I, alkoxy of 1 to 6 carbons, or fluoroalkoxy of 1 to 6 carbons;
m is an integer 0 to 3;
o is an integer 0 to 4;
n is 0–5;
Y is phenyl, naphthyl, or a heteroaryl group selected from a group consisting of pyridyl, thienyl, furyl, pyridazinyl, pyrimidinyl, pyrazinyl; oxazolyl, thiazolyl, or imidazolyl;
B is COOH, a pharmaceutically acceptable salt thereof, $CONR_6R_7$ or $COOR_8$ where $R_6$ and $R_7$, independently, are hydrogen or an alkyl group of 1 to 6 carbons and $R_8$ is alkyl of 1 to 6 carbons; and
co-administering to said mammal with said compound another chemotherapeutic agent effective for the treatment of the malignant disease or condition of the mammal wherein said composition in combination with interferon.

5. A method in accordance with claim 4 where the chemotherapeutic agent is human recombinant interferon α, human recombinant interferon β, or human recombinant interferon γ.

6. A method of treating a malignant disease or condition in a mammal in need of such treatment, said condition being selected from the group consisting of breast cancer and leukemia, the method comprising the steps of: administering to said mammal a pharmaceutical composition comprising a pharmaceutically acceptable excipient and a therapeutically effective dose of a compound of the formula where $R_1$ is H or methyl, $R_3$ is H or methyl, and $R^*_8$ is H, or lower alkyl of 1 to 3 carbons; or a pharmaceutically acceptable salt of said compound, and co-administering to said mammal with said compound another chemotherapeutic agent effective for the treatment of the malignant disease or condition of the mammal wherein said composition in combination with interferon.

7. A method in accordance with claim 6 where the chemotherapeutic agent is human recombinant interferon a, human recombinant interferon β, or human recombinant interferon γ.

8. A method of treating a malignant disease or condition in a mammal in need of such treatment, said disease or condition being selected from the group consisting of breast cancer and leukemia, the method comprising the steps of: administering to said mammal a pharmaceutical composition comprising a pharmaceutically acceptable excipient and a therapeutically effective dose of a compound of the formula where $R_8$ is H, alkyl of 1 to 3 carbons; or a pharmaceutically acceptable salt of said compound, and
co-administering to said mammal with said compound another chemotherapeutic agent effective for the treatment of the malignant disease or condition of the mammal where the co-administered agent is interferon.

9. A method in accordance with claim 8 where the chemotherapeutic agent is human recombinant interferon α, human recombinant interferon β, or human recombinant interferon γ.

* * * * *